United States Patent [19]
Fujieda et al.

[11] Patent Number: 6,011,860
[45] Date of Patent: Jan. 4, 2000

[54] SMALL RELIABLE IMAGE INPUT APPARATUS INCORPORATED IN FINGERPRINT COLLATION SYSTEM OF PERSONAL IDENTIFICATION

[75] Inventors: Ichiro Fujieda; Michihisa Suga, both of Tokyo, Japan

[73] Assignee: NEC Corporation, Tokyo, Japan

[21] Appl. No.: 09/020,908

[22] Filed: Feb. 9, 1998

[30] Foreign Application Priority Data

Feb. 12, 1997 [JP] Japan ................................. 9-028060
Jul. 2, 1997 [JP] Japan ................................. 9-191998

[51] Int. Cl.[7] ........................................... G06K 9/00
[52] U.S. Cl. ............................ 382/126; 382/124
[58] Field of Search ......................... 382/100, 115, 382/116, 120, 123, 124, 125, 126, 127, 190, 260; 356/71, 283, 284

[56] References Cited

U.S. PATENT DOCUMENTS

| | | | |
|---|---|---|---|
| 5,073,949 | 12/1991 | Takeda et al. | 382/115 |
| 5,621,516 | 4/1997 | Shinzaki et al. | 382/124 |
| 5,650,842 | 7/1997 | Maase et al. | 382/124 |

FOREIGN PATENT DOCUMENTS

| | | | |
|---|---|---|---|
| 63-301368 | 12/1988 | Japan | G06F 15/64 |
| 2-259969 | 10/1990 | Japan | G06F 15/62 |
| 3-256185 | 11/1991 | Japan | G06K 9/00 |

*Primary Examiner*—Jose L. Couso
*Assistant Examiner*—Duy M. Dang
*Attorney, Agent, or Firm*—Young & Thompson

[57] ABSTRACT

An image input device has a optical guide plate exposed to a window of a photo-shield case, a pair of light emitting diodes attached to side surfaces of the optical guide plate for radiating light into it, an area image sensor provided under the optical guide plate, a gradient index lens unit provided between the optical guide plate and the area image sensor and a filter connected to the area image sensor for eliminating a low frequency component from an image carrying signal; when a person presses a finger on the optical guide plate, the fingerprint scatters the light toward the gradient index lens unit, and the area image sensor produces the image carrying signal from the incident light; the reflection on valley lines is gradually varied along the width of the finger, and the elimination of the low frequency component makes the contrast of the image clear.

27 Claims, 9 Drawing Sheets

SMALL RELIABLE IMAGE INPUT APPARATUS INCORPORATED IN FINGERPRINT COLLATION SYSTEM OF PERSONAL IDENTIFICATION

FIELD OF THE INVENTION

This invention relates to a fingerprint collation system of personal identification and, more particularly, to a small reliable image input apparatus incorporated in the fingerprint collation system of personal identification.

DESCRIPTION OF THE RELATED ART

The personal identification is an important technology for a personal information network system such as a banking system handling electronic money. Biological information is suitable for the personal identification. Especially, the fingerprint gives a piece of personal biological information, and the piece of personal biological information is reliable. Moreover, the image of fingerprint is so small that a personal identification system obtains it through a small image input apparatus. In fact, a fingerprint collation system has been already used in criminal investigation and an admission checking system.

A personal computer and a portable telephone are getting popular and popular in the society, and the fingerprint collation technology is expected to check a person to see whether or not he or she is allowed to use it. However, the image input apparatus for the fingerprint is usually large and expensive, and it is difficult to incorporate the fingerprint collation technology in the personal system.

Japanese Patent Publication of Unexamined Application No. 3-256185 proposes a small image input device available for the personal fingerprint collation technology. FIG. 1 illustrates the prior art image input device disclosed in the Japanese Patent Publication of Unexamined Application. The prior art image pickup device comprises an optical guide plate 1, a light source 2 radiating an optical beam 3 to a light entry port 1a of the optical guide plate 1 and an image pickup device 4 provided under the optical guide plate 1. The optical guide plate 1 propagates incident light 5 therealong, and the incident light 5 repeats the total reflection in the optical guide plate 1 during the propagation.

When a person puts a finger 6 on the optical guide plate 1, the incident light 5 illuminates the fingerprint 6a. Although the ridges 6b of the fingerprint 6a are held in contact with the upper surface of the optical guide plate 1, the valleys 6c of the fingerprint 6a are spaced from the upper surface, and only the ridges 6b scatters the light 5 toward the image pickup device 4. For this reason, the reflected light 7 carries the image of the fingerprint 7, and is incident onto the image pickup device 4.

Another image input device 10 is disclosed in Japanese Patent Publication of Unexamined Application No. 2-259969, and FIG. 2 illustrates the prior art image input device 10 incorporated in a fingerprint collation system. The image input device 10 comprises an optical guide plate 11 implemented by a glass plate, a light source 12 provided at one end of the optical guide plate 11, a personal identification circuit 13 optically connected to the optical guide plate 11, a light receiver 14 provided under the optical guide plate 11, a lens unit 15 and an optical filter 16 provided between the optical guide plate 11 and the light receiver 14. The light receiver 14 is connected to a biological information discriminator 17, and the biological information discriminator 17 checks reflected light 18 to see whether or not the light 18 is reflected from a living body. The biological information discriminator 17 is connected to the personal identification circuit 13, and supplies a discriminating signal DS1 representative of the result of discrimination.

The prior art image input device functions as follows. While a person is not putting his finger 19 on the upper surface of the optical guide plate 11, the light source 12 radiates light 20 toward the optical guide plate 11, and the optical guide plate 11 propagates the light 20 toward the personal identification circuit 13 through repetition of total reflection. The light 20 is incident onto the personal identification circuit 13 without substantial loss.

On the other hand, when the person presses the finger 19 against the upper surface of the optical guide plate 11, the fingerprint partially breaks the conditions of the total reflection. The ridge lines of the fingerprint scatters the light 20, but the valley lines of the fingerprint allow the light 20 to proceed toward the personal identification circuit 13. Thus, the light 20 carries the image of the fingerprint, and the personal identification circuit 13 recognizes the contrast representative of the fingerprint.

The fingerprint scatters the light 20 toward the lens unit 15, and the scattered light passes through the lens unit 15 and the optical filter 16. The scattered light falls onto the light receiver 14, which gives an electric signal proportional to the intensity of the scattered light. The electric signal is supplied to the biological information discriminator 17, and checks the image to see whether the light 20 is scattered on a finger of a living body or a replica thereof. If the finger 19 is a part of a living body, the intensity of the scattered light is varied with the pressure against the optical guide plate 11, and the variation is unique to the living body. For this reason, the biological information discriminator 17 watches the intensity of the scattered light represented by the electric signal 14 to see whether or not the variation guarantees the finger to be a part of a living body or a replica.

If the biological information discriminator 17 determines the finger to be a part of a living body, the biological information discriminator 17 supplies the discriminating signal DS1 to the personal identification circuit 13, and the personal identification circuit 13 starts the collation. On the other hand, if the finger is a replica, the discriminating signal DS1 is representative of the fact, and the personal identification circuit 13 does not carry out the collation.

The first prior art disclosed in Japanese Patent Publication of Unexamined Application No. 3-256185 encounters problems in large dimensions, poor contrast and defenseless against a replica. The light source radiates parallel light 3, and the optical guide plate 1 requires the light entry port 1a such as a prism. Moreover, relatively long optical path is required for the image pickup device 4. For this reason, the first prior art occupies large space. The poor contrast is derived from the background light and reflection from the valleys 6c. When the first prior art image input device is placed in the light, the background light passes through the optical guide plate, and is incident on the image pickup device 4. The background light makes the contrast poor. Thus, the prior art image input device is not reliable. Moreover, when the ridges 6b scatters the light 5, part of the light 5 is scattered toward the valleys 6c, and is reflected on the inner surfaces of the valleys 6c. The reflected light passes through the optical guide plate 1, and is incident on the image pickup device. The reflected light also makes the contrast poor. The poor contrast makes the fingerprint collation system to fail to exactly discriminate the fingerprint, and the prior art image input device is not reliable due to the poor contrast. There is not any protection against a replica, and the first image input device is not reliable.

On the other hand, the second prior art disclosed in Japanese Patent Publication of Unexamined Application No. 2-259969 encounters problems in large dimensions and insufficient protection against a replica. An image sensor (not shown) is incorporated in the personal identification circuit, and is spaced from the area where the finger is pressed. Moreover, the lens unit 15, the optical filter 16, the light receiver 14 and the biological information discriminator 17 are required for the protection against a replica, and those components make the prior art image input device large and expensive. The protection against a replica is based on the variation of the intensity of the—scattered light. If a replica is prepared so that it varies the intensity of the scattered light with time, the biological information discriminator 17 misunderstands the image to represent a fingerprint of a living body. Thus, the protection is insufficient, and the second prior art image input device is not reliable.

SUMMARY OF THE INVENTION

It is therefore an important object of the present invention to provide a small image input device.

It is also an important object of the present invention to provide an image input device, which emphasizes the contrast of an image so as to clearly discriminate it.

It is also an important object of the present invention to provide a reliable image input device, which clearly discriminates a piece of biological information from a piece of non-biological information.

In accordance with one aspect of the present invention, there is provided an image input device for producing a piece of data information representative of a fingerprint of a finger of a living body comprising a transparent optical guide plate including a first surface having an detecting area where the living body presses the finger and radiating a reflection representative of an image of the fingerprint from a second surface to the outside thereof, a light source attached to an incident area of a third surface of the transparent optical guide plate narrower than the detecting area and diffusing light into the transparent optical guide in such a manner as to illuminate the detecting area, an image pickup device provided in the vicinity of the second surface and having an incident surface so as to detect the reflection, an image forming means provided between the second surface and the image pickup device so as to form the image on the incident surface and a case for accommodating the transparent optical plate, the light source, the image pickup device and the image forming mean.

In accordance with another aspect of the present invention, there is provided an image input device for producing a piece of data information representative of a fingerprint of a finger of a living body comprising a transparent optical guide plate including a first surface having an detecting area where the living body presses the finger and radiating a reflection representative of an image of the fingerprint from a second surface to the outside thereof, a light source radiating light into the transparent optical guide so as to illuminate the detecting area, an image pickup device provided in the vicinity of the second surface and having an incident surface so as to detect the reflection, a gradient index lens array provided between the second surface and the image pickup device so as to form the image on the incident surface and a case for accommodating the transparent optical plate, the light source, the image pickup device and the image forming mean.

In accordance with yet another aspect of the present invention, there is provided an image input device for producing a piece of data information representative of a fingerprint of a finger of a living body comprising a transparent optical guide plate including a first surface having an detecting area where the living body presses the finger and radiating a reflection representative of an image of the fingerprint from a second surface to the outside thereof, a light source radiating light into the transparent optical guide so as to illuminate the detecting area, an image pickup device provided in the vicinity of the second surface and having an incident surface so as to detect the reflection, an image forming means provided between the second surface and the image pickup device so as to form the image on the incident surface, a case for accommodating the transparent optical plate, the light source, the image pickup device and the image forming mean and an eliminating means for eliminating a sub-piece of data information representative of a sub-image of valley lines of the fingerprint from the piece of data information representative of the fingerprint.

In accordance with still another aspect of the present invention, there is provided an image input device for producing a piece of data information representative of a finger comprising a transparent optical guide plate including a first surface having an detecting area where the fingerprint is pressed and radiating a reflection representative of an image of the fingerprint from a second surface to the outside thereof, a light source radiating light into the transparent optical guide so as to illuminate the detecting area, an image pickup device provided in the vicinity of the second surface and having an incident surface so as to detect the reflection, a gradient index lens array provided between the second surface and the image pickup device so as to form the image on the incident surface, a case for accommodating the transparent optical plate, the light source, the image pickup device and the image forming mean and a biological information discriminating means checking the reflection to see whether or not the finger changes its reflection with time so as to produce another piece of data information representative of a living body or non-living body.

BRIEF DESCRIPTION OF THE DRAWINGS

The features and advantages of the image input device will be more clearly understood from the following description taken in conjunction with the accompanying drawings in which.

DESCRIPTION OF THE PREFERRED EMBODIMENTS

First Embodiment

Figure 1:
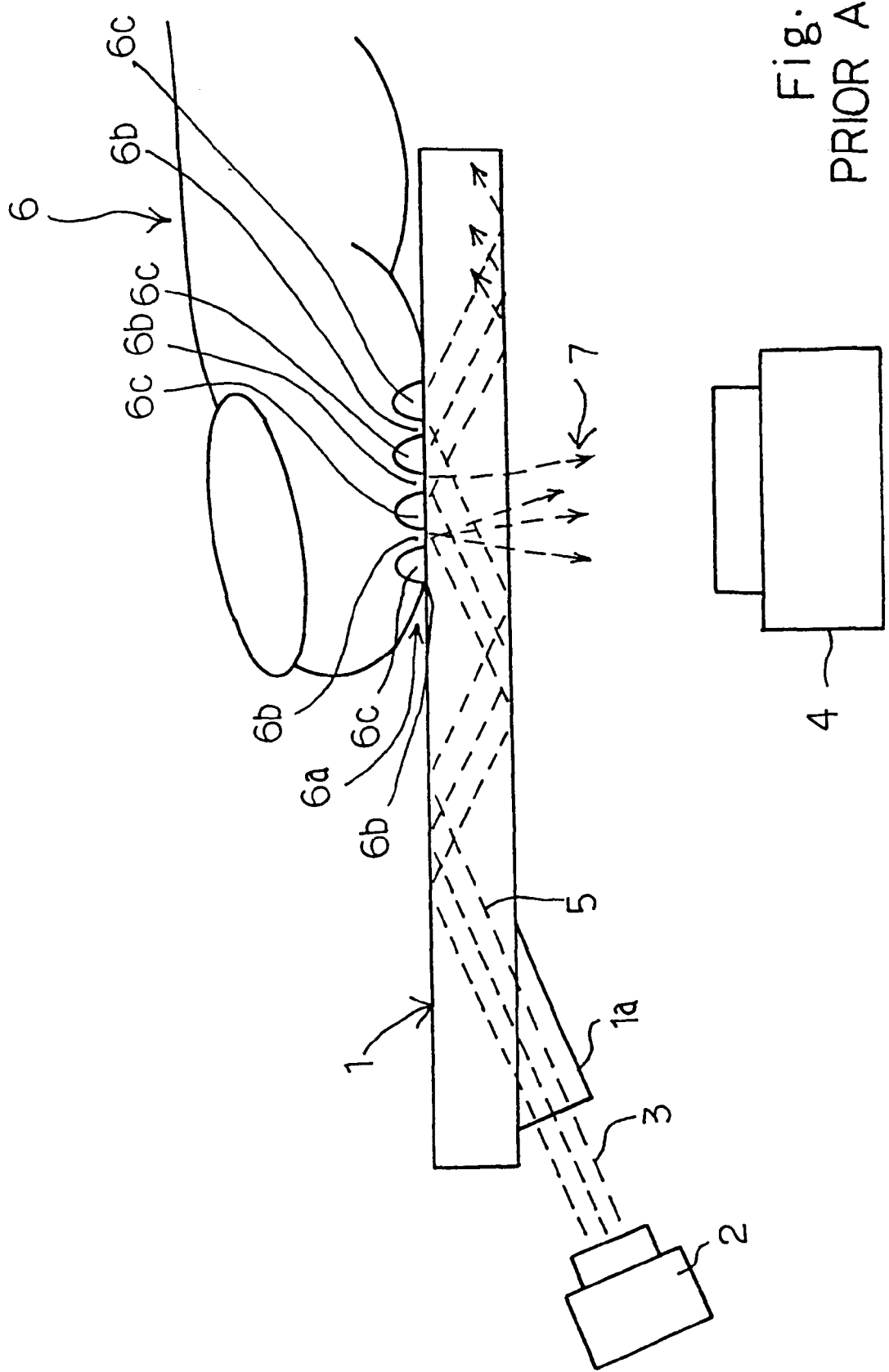
FIG. 1 is a schematic view showing the prior art image input device disclosed in Japanese Patent Publication of Unexamined Application No. 3-256185.
Figure 2:
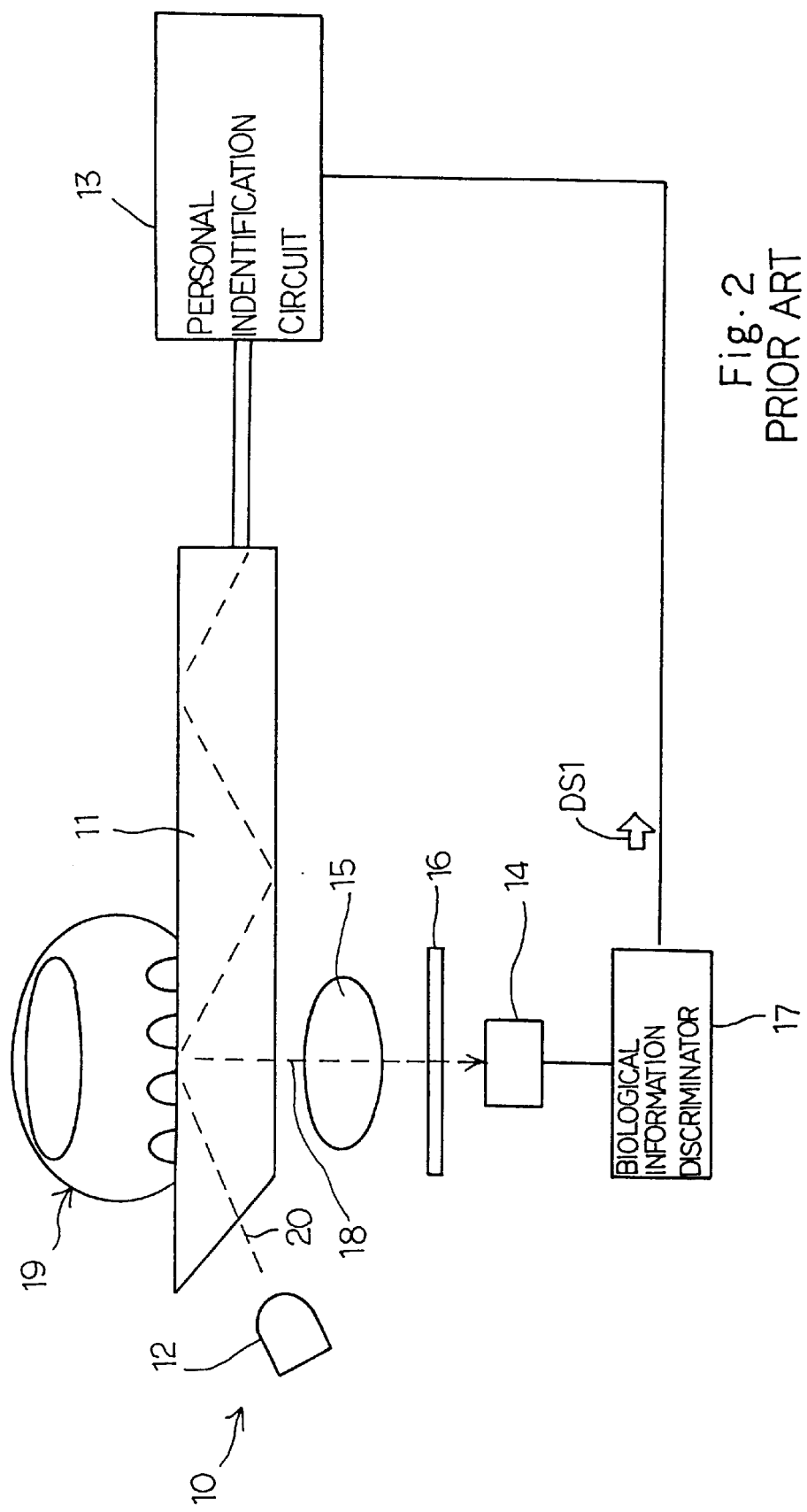
FIG. 2 is a schematic view showing the prior art image input device disclosed in Japanese Patent Publication of Unexamined Application No. 2-259969.
Figure 3:
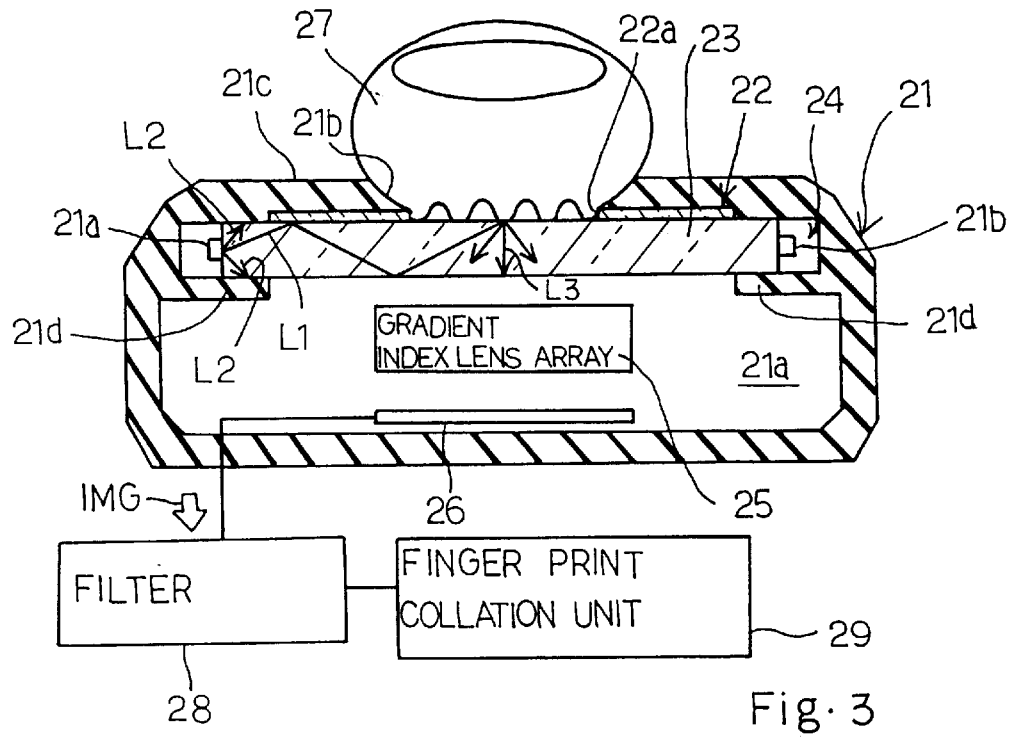
FIG. 3 is a cross sectional view showing the structure of an image input device according to the present invention.

Referring to FIG. 3 of the drawings, an image input device embodying the present invention largely comprises a photo-shield case 21, a low refractive layer 22 provided inside of the photo-shield case 21, an optical guide plate 23 also provided inside of the photo-shield case 21, a light source 24 associated with the optical guide plate 23, a gradient index lens array 25 and an area image sensor 26. The light source 24 is attached to the side surfaces of the optical guide plate 23, and the gradient index lens array 25 and the area image sensor 26 are provided under the optical guide plate 23.

The photo-shield case 21 has an inner space 21a, and an opening 21b is formed in the upper portion 21c of the photo-shield case 21. The shape of the opening 21b is like a finger 27, and the upper portion 21c guides the finger 27 onto the optical guide plate 23. The photo-shield case 21 is formed of photo-absorbing material such as, for example, black synthetic resin or anodized aluminum layer, and prevents the inner space 21a from being illuminated by the external light. A pair of guide plates 21d inwardly projects from the inner surface of the photo-shield case 21, and the optical guide plate 23 is fixed to a predetermined position on the pair of guide plates 21d.

The optical guide plate 23 is located under the opening 21b, and the low refractive layer 22 is inserted between the upper portion 21c and the optical guide plate 23. The optical guide plate 23 is formed of transparent glass or transparent hard synthetic resin, and is regulated to 1 millimeter to 3 millimeters in thickness. An opening 22a is also formed in the low refractive layer 22, and is nested in the opening 21b in the upper portion 21c. The low refractive layer 22 defines a detecting area 23a exposed to the opening 22a. For this reason, the finger 27 is directly pressed against the detecting area 23a of the optical guide plate 23. The low refractive layer 22 is smaller in refraction index than the optical guide plate 23, and may be formed of the air. The refraction index of the air is 1, and is surely smaller than the refraction index of the transparent material of the optical guide plate 23.

Figure 4:
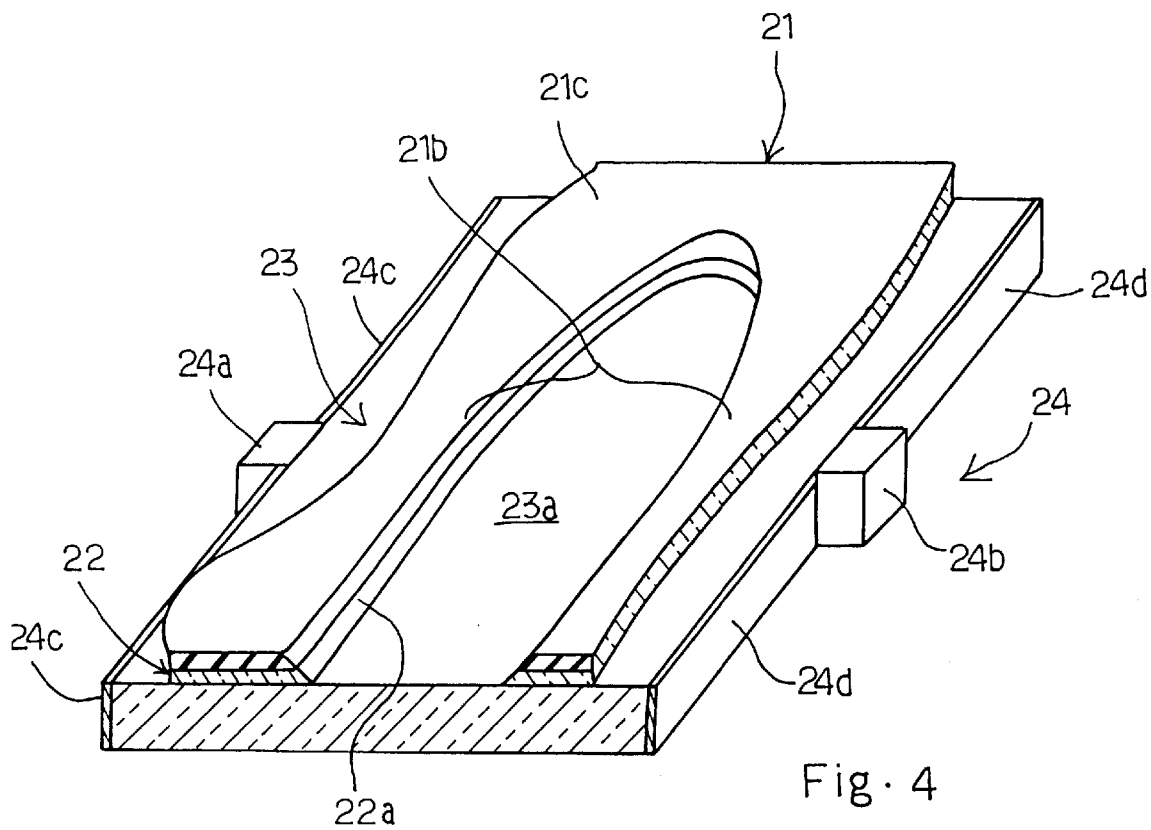
FIG. 4 is a perspective view showing essential parts of the image input device shown in FIG. 3.

As will be better seen from FIG. 4, the light source 24 includes a pair of light emitting diodes 24a/24b and reflecting layers 24c/24d. The light emitting diodes 24a/24b are in the form of discrete semiconductor chip, and are directly attached to both side surfaces of the optical guide plate 23. The remaining side surfaces are covered with the reflecting layers 24c/24d. The light emitting devices 24a/24b radiate light L1 into the optical guide plate 23, and the reflecting layers 24c/24d reflect the light L1 without radiation toward the outside. Thus, the reflecting layers 24c/24d confines the light L1 in the optical guide plate 23, and improves the utilization factor of the light 23. The guide plates 21d are held in contact with the optical guide plate 23 around the light emitting diodes 24a/24b, and the guide plates 21d reflect light component L2 incident upon the upper/lower surfaces of the optical guide at large angle.

The gradient index lens array 25 is an image forming optical system, and a plurality of gradient index lenses are two-dimensionally arranged. The area image sensor 26 is adjusted to the image forming plane of the gradient index lens array 25, and forms an erect image at magnification ratio of 1. The area image sensor 26 is implemented by a solid state image pickup device such as, for example, a two-dimensional charge coupled device fabricated on a crystalline silicon chip or a MOS image sensor fabricated on a glass plate by the thin film semiconductor technology. The area image sensor 26 converts pattern of the incident light to an image carrying signal IMG.

The image input device embodying the present invention further comprises a filter 28. The area image sensor 26 is connected to the filter 28, and the filter 28 eliminates a low-frequency component from the image carrying signal IMG. After the elimination of the low frequency components, the filter 28 supplies the image carrying signal IMG to a fingerprint collation unit 29. The filter 28 and the fingerprint collation unit 29 may be implemented by independent circuits. Alternatively, a data processing unit and suitable software may form the filter 28 and the fingerprint collation unit 29.

In this instance, a data processing system and a program sequence executed by the data processing system as a whole constitute the filter 28. The filter 28 carries out the Fourier transformation on the image carrying signal IMG, and decreases the Fourier coefficient of the low frequency component to zero. Thereafter, the filter 28 carries out the inverse Fourier transformation so as to restore the image carrying signal IMG without the low frequency component.

The gradient index lens array 25 has a conjugate length, i.e., the distance between the object and the image forming plane, equal to or less than 5–10 millimeters, and, accordingly, the photo-shield case 21 is designed to be of the order of 10–15 millimeters thick. Moreover, the light emitting diodes 24a/24b measure 1 millimeter to 3 millimeters long, and are much shorter than the detecting area 23a. The detecting area 23a is as wide as the finger 27 placed thereon, and measures 20 millimeters to 30 millimeters. For this reason, the photo-shield case 21 and, accordingly, the image input device are much smaller than the prior art image input devices. In this instance, the photo-shield case 21 is 20 millimeters in width, 30 millimeters in length and 15 millimeters in height.

The component elements 21 to 26 of the image input device are not expensive, and the production cost is lower than those of the prior art image input devices.

Only the detecting area 23a is exposed to the outside, and the inner space 21a is photo shielded by the photo-shield case 21. For this reason, when the finger 27 is pressed against the detecting area 23a, any light is hardly incident from the outside onto the inner space 21a, and the area image sensor 26 detects only the scattered light L3 from the fingerprint. For this reason, the contrast of the image is drastically improved. Moreover, the photo-shield case 21 absorbs the light L3, and does not allow the light L3 to be radiated therefrom as stray light.

The image input device functions behaves as follows. The light emitting diodes 24a/24b are powered, and the light L1 is incident onto the optical guide plate 23. The light L1 has wide directivity, and the optical guide plate 23 is contiguous to the low refractive layer 22 along the upper surface thereof and to the air along the lower surface thereof. For this reason, most of the light L1 repeats the total reflection on the upper/lower surfaces of the optical guide plate 23. Even if a small mount of light L1 is leaked from the optical guide plate 23, the leakage light is absorbed by the photo-shield case 21.

Assuming now that the finger 27 is pressed against the detecting area 23a, the light L1 is scattered on the ridge lines of the fingerprint, and the scattered light L3 is partially taken out from the optical guide plate 23. The scattered light L3 carries an image of the fingerprint, and the gradient index lens array 25 forms the image on the area image sensor 26.

Figure 5:
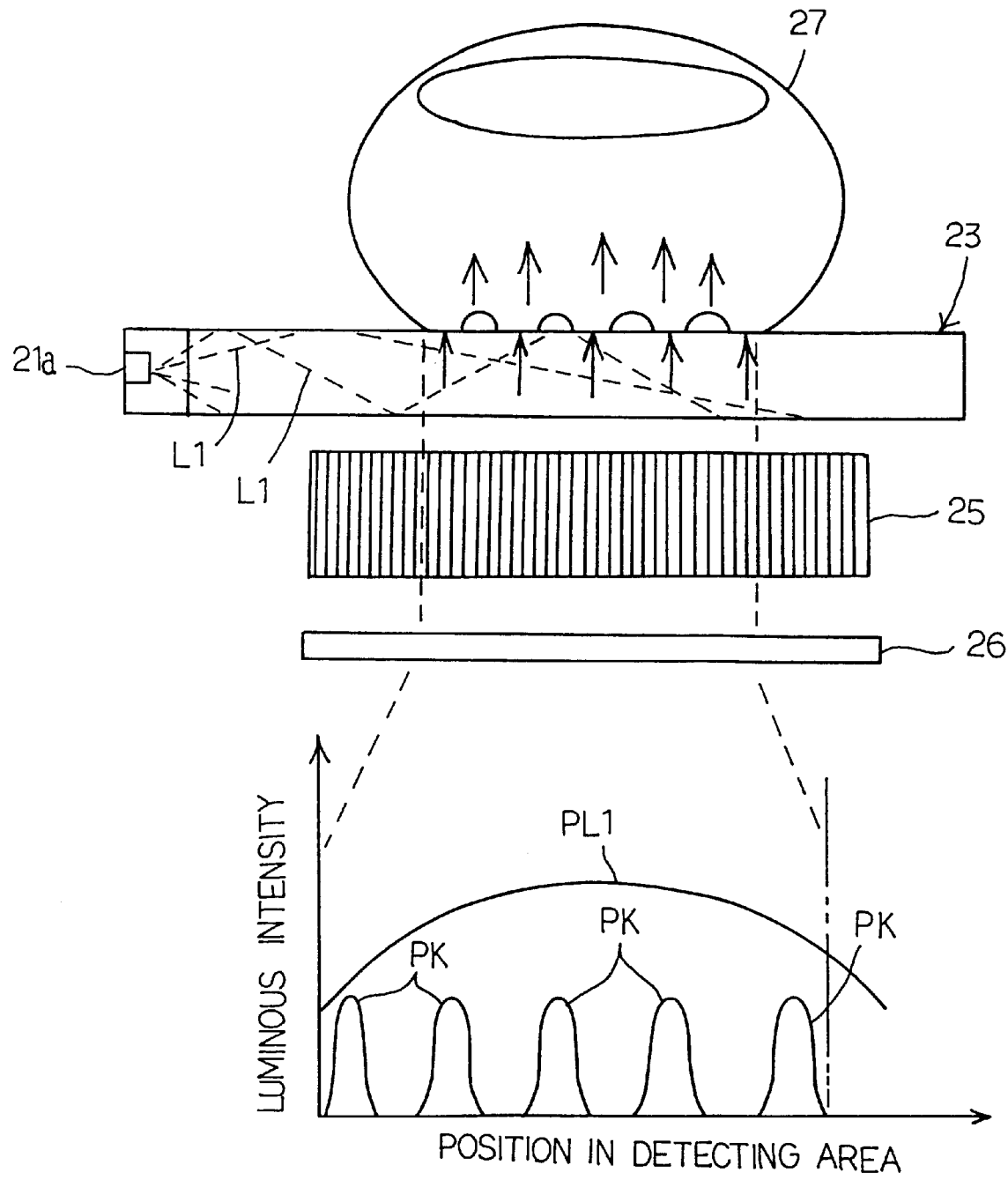
FIG.5 is a drawing showing the imaging principle for the image input device shown in FIG. 3.

FIG. 5 illustrates a distribution of luminous intensity detected on the image sensor 26. The light L1 is scattered by the ridge lines of the fingerprint, and the gradient index lens unit 25 forms an image of the fingerprint on the image sensor 26. The image has strong luminous intensity corresponding to the ridge lines and weak luminous intensity corresponding to the valley lines. For this reason, the image carrying signal IMG has peaks PK representative of the ridge lines. Part of the light scattered by the ridge lines is incident on the skin forpheming the valley lines, and is scattered thereon. The light scattered inside the finger is partially incident onto the gradient index lens array 25, and is guided to the area image sensor 26. The amount of light scattered inside the finger in the central area of the finger is more than the amount of light scattering in the peripheral areas of the finger, and the luminous intensity of the light scattered inside the finger is plotted as indicated by a curve PL1. The light scattered on the ridge lines has a high spatial frequency corresponding to the intervals of the ridge lines, and the light scattered inside the finger a low spatial frequency corresponding to the width of the finger 27. Amorphous silicon may be used for the image sensor material. The image sensor 26 converts the light from both ridge and valley lines, and the image carrying signal IMG represents the contrast of the order of 1.3.

The filter 28 eliminates the low frequency component corresponding to the low spatial frequency representative of the scattering on the valley lines from the image carrying signal IMG, and emphasizes the ridge lines. Thus, the filter 26 improves the contrast of the image of the fingerprint, and serves as an eliminating means.

Figure 6:
FIG. 6 is a view showing the image of a fingerprint detected by an area image sensor.
Figure 7:
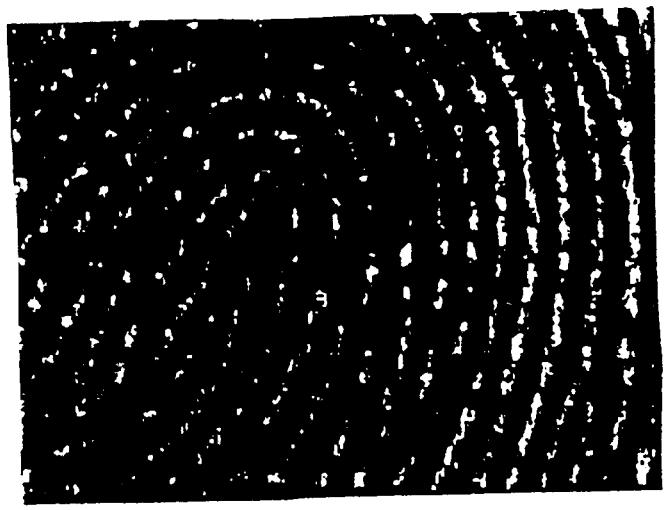
FIG. 7 is a view showing the image of the fingerprint represented by an image carrying signal after elimination of a low frequency component.

FIG. 6 illustrates the image of a fingerprint incident on the area image sensor 26, and FIG. 7 illustrates the image of the fingerprint after the elimination of the low frequency component. As will be understood from comparison between the images, the contrast between the ridge lines and the valley lines is emphasized in FIG. 7, and, accordingly, the image shown in FIG. 7 is more appropriate for the fingerprint collation rather than the image shown in FIG. 6.

Figure 8:
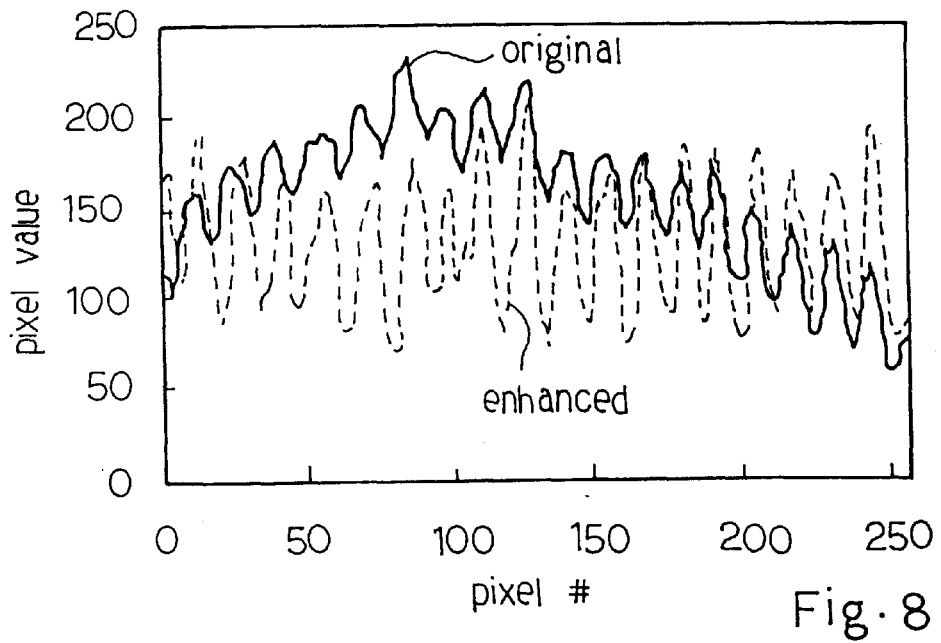
FIG. 8 is a graph showing the contrast of the images.

FIG. 8 shows the variation of the luminous intensity, which is referred to as "pixel value", along a horizontal line of the images shown in FIGS. 6 and 7. Plots "original" shows the variation along the horizontal line in FIG. 6, and plots "enhanced" shows the variation after the elimination of the low frequency component. Plots "original" teaches that the contrast is of the order of 1.3, and the pixel value is longer in the central area of the finger due to the scattering inside the finger. After the elimination of the low frequency component, the contrast is enhanced as clearly seen by the plots "original".

In this instance, the light emitting diodes 24a/24b is expected to radiate the light L1 in such a manner as to cover the detecting area 23a. A standard light emitting diode emits the light over ±60 degrees, and the detecting area 23a is of the order of 30 millimeters in the longitudinal direction thereof. For this reason, when the light emitting diodes 24a/24b are located at the intermediate position of the detecting area 23a, the light emitting diodes 24a/24b can illuminate the detecting area 23a. The light emitting diodes 24a/24b are so small that the manufacturer can scale down the image input device.

Second Embodiment

Figure 9:
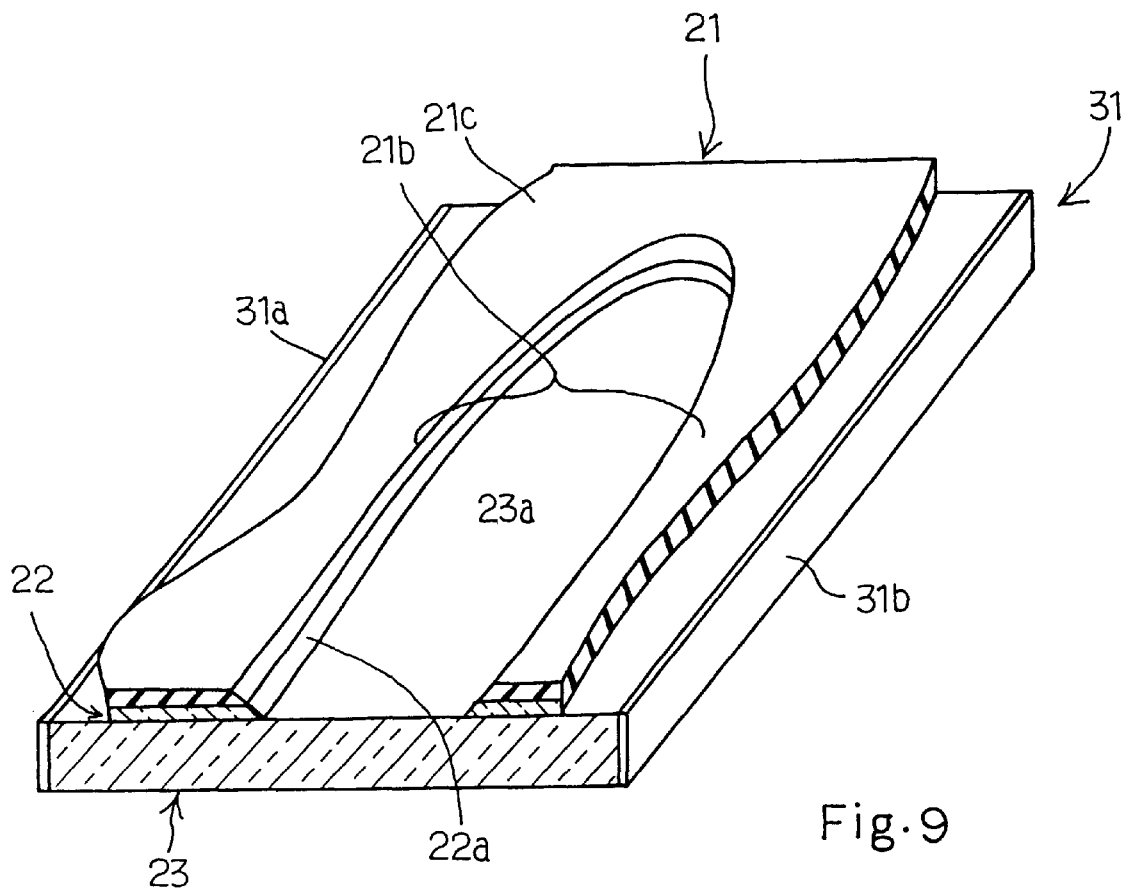
FIG. 9 is a perspective view showing the structure of essential components incorporated in another image input device according to the present invention.

FIG. 9 illustrates components of another image input device embodying the present invention. The image input device implementing the second embodiment is similar to the first embodiment except for a light source 31. For this reason, the other components are labeled with the same references designating corresponding components of the first embodiment without detailed description. Although the gradient index lens array 25, the area image sensor 26 and the filter 28 are also incorporated in the image input device implementing the second embodiment, they are omitted from FIG. 9 for the sake of simplicity.

The light source 31 is implemented by a pair of electro-luminescence plates 31a/31b, and the electro-luminescence plates 31a/31b are attached to side surfaces of the optical guide plate 23. The electro-luminescence plate 31a/31b is fabricated on a glass plate, and has a laminated structure of a transparent electrode of indium-tin-oxide, an organic layer and a reflecting electrode of aluminum, by way of example. When potential of the order of 5 volts is applied to the laminated structure, the electro-luminescence plates 31a/31b emit high-luminous intensity light, and the high-luminous intensity light has a wide angular distribution ranging between ±45 degrees and ±60 degrees. For this reason, the electro-luminescence plates 31a/31b similarly supply the light to the optical guide plate 23. The electro-luminescence plates 31a/31b are equal to or less than 1 millimeter thick, and make the image input device small.

Third Embodiment

Figure 10:
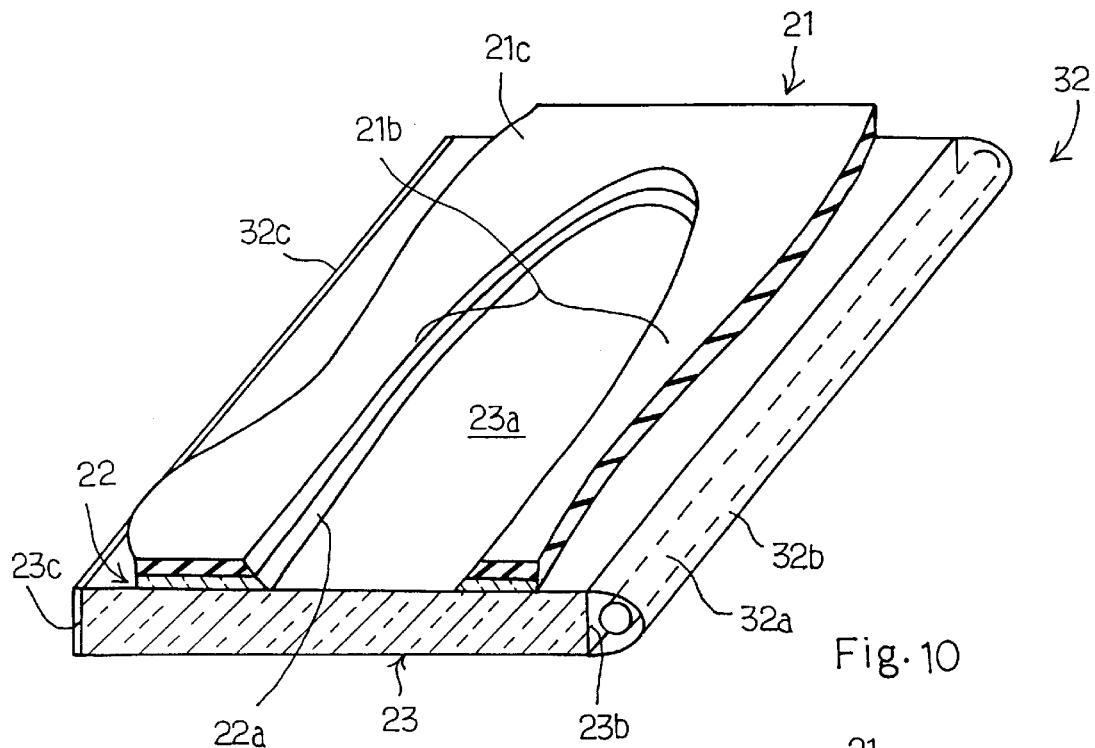
FIG. 10 is a perspective view showing the structure of essential components incorporated in yet another image input device according to the present invention.

FIG. 10 illustrates components of yet another image input device embodying the present invention. The image input device implementing the third embodiment is similar to the first embodiment except for a light source 32. For this reason, the other components are labeled with the same references designating corresponding components of the first embodiment without detailed description. Although the gradient index lens array 25, the area image sensor 26 and the filter 28 are also incorporated in the image input device implementing the third embodiment, they are omitted from FIG. 9 for the sake of simplicity.

The light source 32 is implemented by a cold cathode tube 32a and reflecting layers 32b/32c. The cold cathode tube 32a and the reflecting layer 32b are attached to a side surface 23b of the optical guide plate 23, and radiates light into the optical guide plate 23. The side surface 23c on the opposite side is covered with the reflecting layer 32c. The cold cathode tube 32a and the reflecting layer 32b can be designed so that it has a wide angular distribution ranging between ±45 degrees and ±60 degrees, and achieves the advantages as similar to the light emitting diodes 24a/24b. The light source 32 is of the order of 3 millimeters thick, and a driving circuit (not shown) is connected to the cold cathode tube 32a.

Fourth Embodiment

Figure 11:
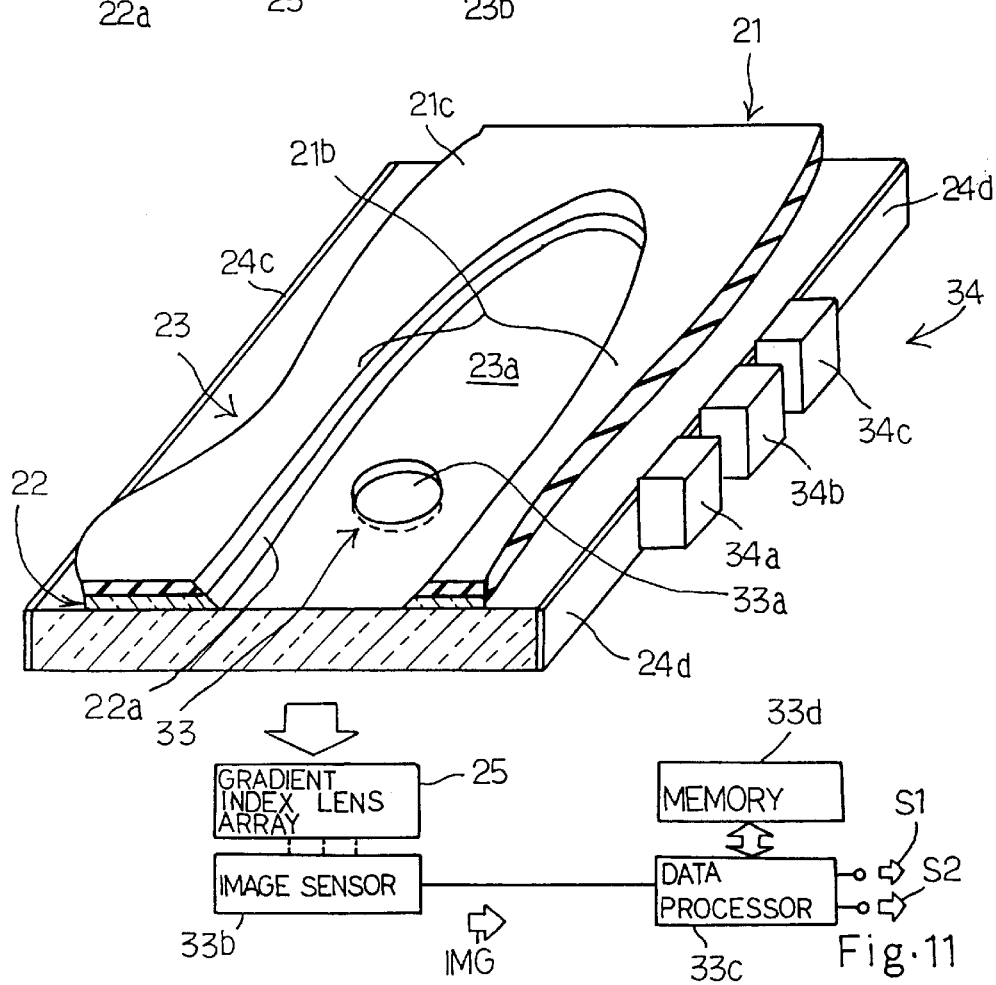
FIG. 11 is a perspective view showing the structure of essential components incorporated in still another image input device according to the present invention.

FIG. 11 illustrates still another image input device embodying the present invention. A biological information discriminating means 33 is incorporated in the image input device implementing the fourth embodiment, and a light source 34 is modified from the light source 24. Other components of the fourth embodiment are labeled with the same references designating corresponding components of the first embodiment.

The light source 34 includes light emitting diodes 34a/34b/34c and the reflecting layers 24c/24d, and the light emitting diodes 34a/34b/34c radiate blue light, green light and red light. Though not shown in FIG. 11, the light emitting diodes 34a/34b/34c are sequentially energized, and the blue light, the green light and the red light are successively radiated to the optical guide plate 23.

The biological information discriminating means 33 includes the light emitting diodes 34a/34b/34c, a recess 33a formed in the optical guide plate 23, an image sensor 33b for a color image, a data processor 33c and a memory 33d. The recess 33a is 3–4 millimeters in diameter and 2–3 millimeters in depth, and is defined by a curved surface.

When a person presses a finger against the detecting area 23a, the finger is held in contact with the flat detecting area 23a, and is spaced from the curved surface within the circular periphery of the recess 33a. The pressure evacuates the blood from the portion on the flat detecting area 23a, and the finger varies its color depending upon a pressure pattern. The finger is partially turned to white on the flat detecting area 23a, and remains red within the circular periphery. The change of color is completed within 10 milliseconds to 100 milliseconds, and is unique to a living body. If a replica is pressed against the detecting area 23a, the color is never changed.

The biological information discriminating means 33 detects the change of color as follows. The light emitting diodes 34a/34b/34c sequentially emit the blue light, the green light and the red light, and the finger reflects the blue light, the green light and the red light toward the gradient index lens array 25. The gradient index lens array 25 forms the image on the image sensor 33b, and the image sensor 33b converts an image on the blue reflection, an image on the green reflection and an image on the red reflection into the image signal IMG. The image signal IMG is supplied to the data processor 33c, and the data processor 33c restores a set of video data representative of the color image of the finger from the image signal IMG after the elimination of the low frequency component. The ridge lines reflects all the light, i.e., the blue light, the green light and the red light, and is seen in white. However, the valley lines reflect the light corresponding to the skin color. For this reason, the change in color is detectable. The set of video data is stored in the memory 33d, and the biological information discriminating means 33 repeats the above-described sequence, and compares the sets of video data to see whether or not the finger partially changes its color. If the charge of color is matched with that of a living body, the data processor 33c produces a signal S1 representative of a living body and a signal S2 representative of the image of fingerprint. On the other hand, if the change of color is different from that of a human body, the data processor 33c produces the signal S1 representative of non-living body.

The color image of the finger contains the biological information more than the variation of reflective index within a narrow range of wavelength, and makes it impossible to use a replica. In fact, it is impossible to make a replica changing its color depending upon the pressure pattern. Thus, the biological information detecting means 33 exactly discriminates the finger of a living body from a replica or a non-living body, and the signal S1 is reliable.

Fifth Embodiment

Figure 12:
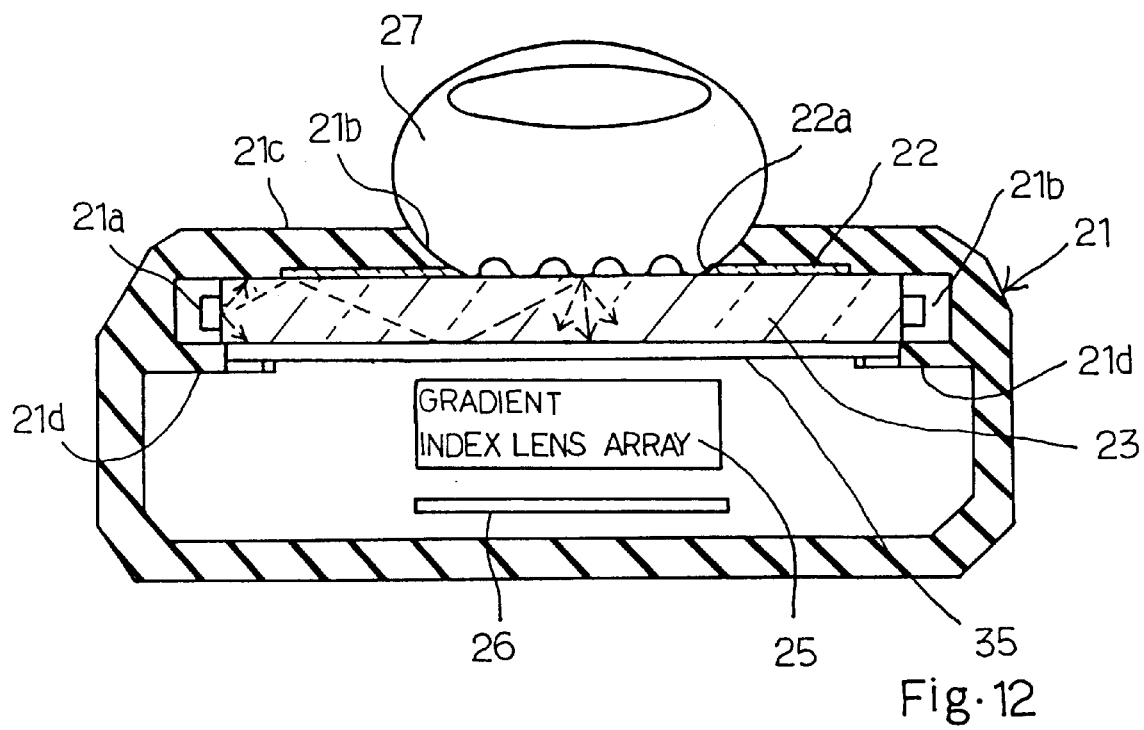
FIG. 12 is a cross sectional view showing the structure of still another image input device according to the present invention.

FIG. 12 illustrates still another image input device embodying the present invention. The image input device implementing the fifth embodiment is similar to the first embodiment except for an anti-reflecting layer 35. For this reason, the other components are labeled with the same references designating corresponding components of the first embodiment.

Figure 13A:
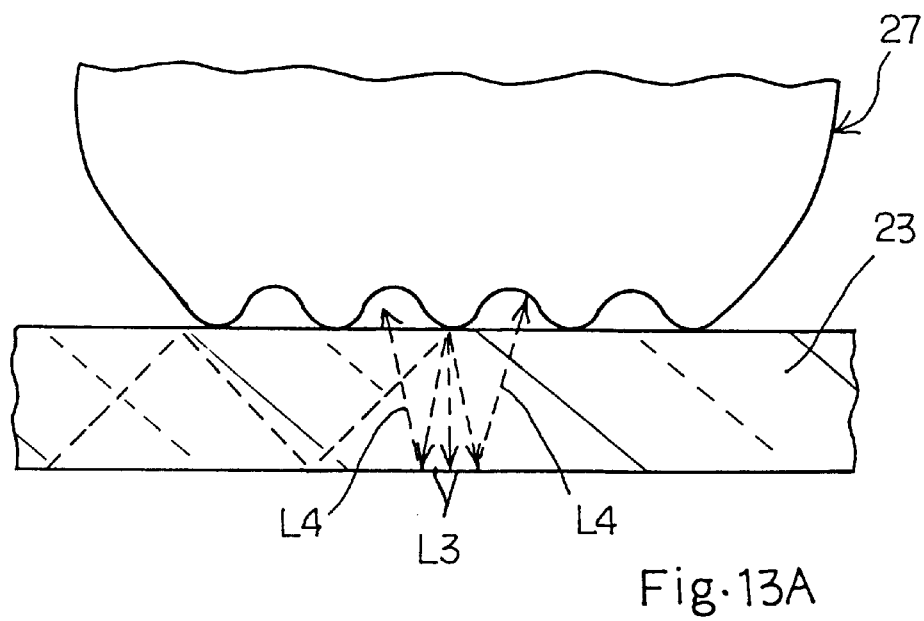
FIGS. 13A and 13B are views showing the behavior of light reflected from a fingerprint.

The anti-reflecting layer 35 is formed of $MgF_2$, $CeO_2$ or $NdO_3$ different in reflective index, and is implemented by a single layer or plural layers on the lower surface of the optical guide plate 23. If any anti-reflecting layer is provided on the lower surface of the optical guide plate 23, the scattered light L3 is reflected on the boundary between the optical guide plate 23 and the air, again, and the reflection L4 illuminates the valley lines of the fingerprint as shown in FIG. 13A. As a result, the reflection L4 is scattered by the valley lines, and is incident on the area image sensor 26. The light component scattered by the valley lines makes the contrast of the image representative of the fingerprint poor.

Figure 13B:
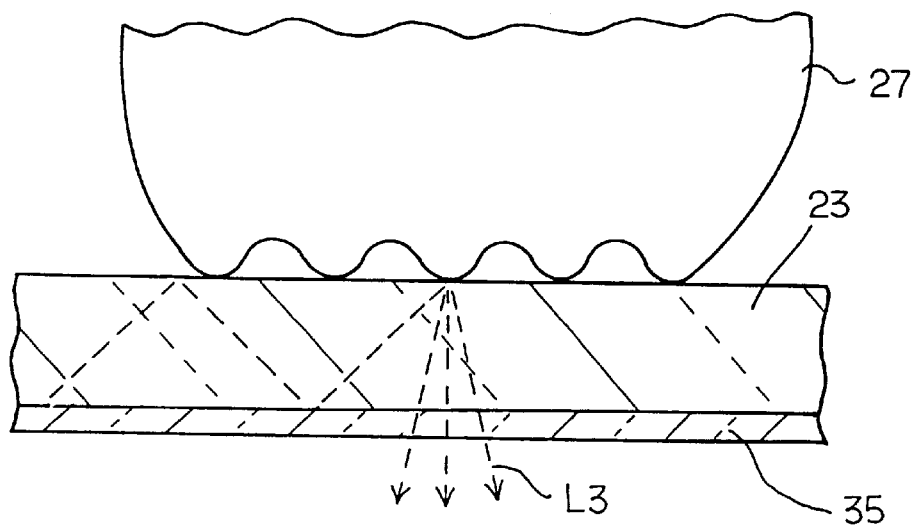

On the other hand, the anti-reflecting layer 35 does not reflect the reflection L3 toward the ridge lines as shown in FIG. 13B, and makes the contrast of the image higher. The anti-reflecting layer 35 serves as an eliminating means.

Sixth Embodiment

Figure 14:
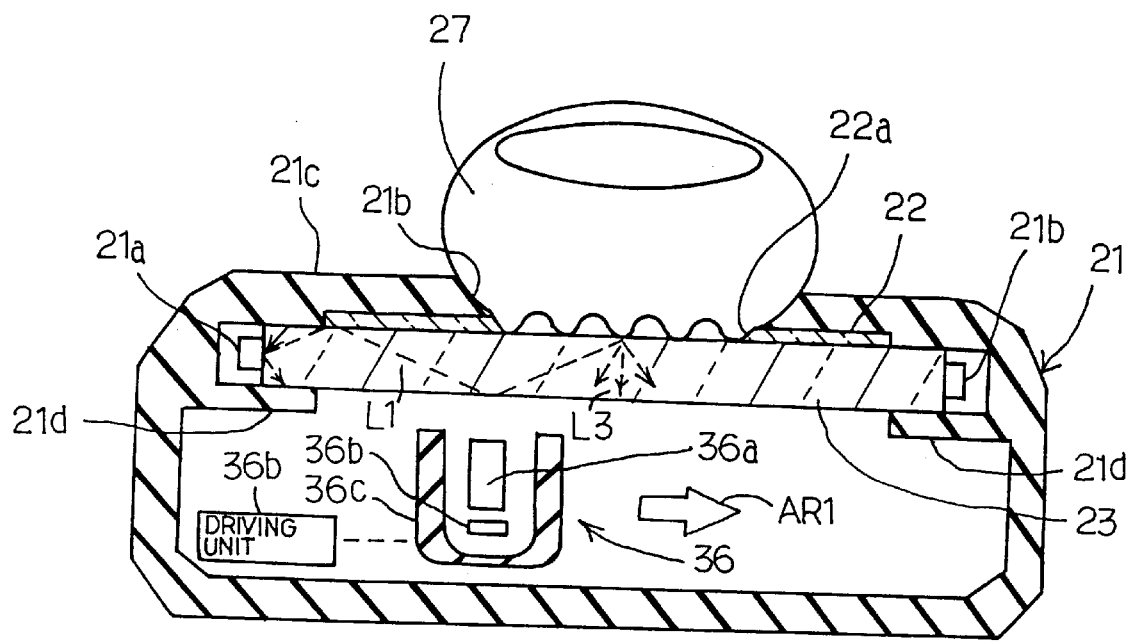
FIG. 14 is a cross sectional view showing the structure of still another image input device according to the present invention.

FIG. 14 illustrates still another image input device embodying the present invention. The image input device implementing the sixth embodiment is similar to the first embodiment except for a movable sensor unit 36. The other components are labeled with the same references designating corresponding components of the first embodiment.

The movable sensor unit 36 includes a linear array 36a of gradient index lenses, a linear image sensor 36b located under the linear array 36a, a carrier 36c accommodating the linear lens array 36a and the linear image sensor 36b and a driving unit 36d reciprocally moving the carrier 36c. The linear lens array 36a is implemented by a plurality of gradient index lenses linearly arranged, and forms an erect image on the linear image sensor 36b at magnification ratio of 1.

When a finger is pressed against the detecting area on the optical guide plate 23, the light is scattered by the ridge lines of the fingerprint, and the scattered light L3 passes through the optical guide plate 23 as similar to the first embodiment. The driving unit 36d moves the carrier 36c in the direction indicated by arrow AR1, and the linear image sensor 36b successively converts the scattered light L3 to the image carrying signal IMG. Although the driving unit 36d is required, the linear lens array 36a and the linear image sensor 36b are economical rather than the two-dimensional gradient index lens array 25 and the area image sensor 26.

As will be appreciated from the foregoing description, the light source is attached to the optical guide plate, and emits the light thereinto so as to illuminate the detecting area. This results in reduction of dimensions.

The gradient index lens unit has a conjugate length equal to or less than 5 to 10 millimeters, and is conducive to the reduction of dimensions. The light source such as a light emitting diode or a electro-luminescence plate and the gradient index lens unit are not expensive, and reduce the production cost of the image input device.

The filter 28 or the anti-reflecting layer 35 suppresses the light scattered by the valley lines from the image representative of the fingerprint, and enhances the contrast of the image. Thus, the image input device produces a high quality image of a fingerprint.

The photo-shield case prevents the image sensor from the external light, and the black inner surface of the photo-shield case absorbs the undesirable stray light. This results in further enhancement of the contrast.

Finally, the image input device monitors local variation of color image of a fingerprint, and exactly discriminates the fingerprint of a living body from a replica. Thus, the image input device according to the present invention is reliable.

Although particular embodiments of the present invention have been shown and described, it will be obvious to those skilled in the art that various changes and modifications may be made without departing from the spirit and scope of the present invention.

For example, the number of light emitting diodes is dependent on the sensitivity of the area sensor 26. If the area sensor 26 is highly sensitive, only one light emitting diode may be attached to the optical guide plate 23. On the other hand, if the area sensor 26 is less sensitive, more than two light emitting diodes may be attached to the optical guide plate 23. The recess 33a may be replaced with a ring slightly projecting from the flat detecting area 23a.

The gradient index lens may be replaced with a Fresnel lens or a suitable prism.

What is claimed is:

1. An image input device for producing a piece of data information representative of a fingerprint of a finger of a living body, comprising:
   a transparent optical guide plate including a first surface having an detecting area where said living body presses said finger, and radiating a reflection representative of an image of said fingerprint from a second surface to the outside thereof;
   a light source attached to an incident area of a third surface of said transparent optical guide plate narrower than said detecting area, and diffusing light into said transparent optical guide in such a manner as to illuminate said detecting area;
   an image pickup device provided in the vicinity of said second surface, and having an incident surface so as to detect said reflection;
   an image forming means provided between said second surface and said image pickup device so as to form said image on said incident surface; and
   a case for accommodating said transparent optical plate, said light source, said image pickup device and said image forming mean.

2. The image input device as set forth in claim 1, in which said light source includes at least one light emitting diode attached to said incident area.

3. The image input device as set forth in claim 2, said light source further includes a first reflecting layer covering a remaining area of said third surface and a second reflecting layer covering a fourth surface of said transparent optical guide plate opposite to said third surface.

4. The image input device as set forth in claim 1, in which said light source includes at least one electro-luminescence plate attached to said third surface.

5. The image input device as set forth in claim 4, in which said light source further includes another electro-luminescence plate attached to a fourth surface of said transparent optical guide plate opposite to said third surface.

6. The image input device as set forth in claim 1, in which said light source includes a cold cathode tube attached to said third surface and a first reflecting layer provided around said cold cathode tube for reflecting light toward said third surface.

7. The image input device as set forth in claim 6, in which said light source further includes a second reflecting layer attached to a fourth surface of said transparent optical guide plate opposite to said third surface.

8. The image input device as set forth in claim 1, in which said case has an inner space photo-shielded from an external light and a window open to the outside of said inner space, and said transparent optical plate, said light source, said image pickup device and said image forming mean are accommodated in said inner space in such a manner that said transparent optical plate is exposed to said window.

9. The image input device as set forth in claim 8, in which said case is colored in black.

10. The image input device as set forth in claim 1, in which said image pickup device is implemented by an area image sensor.

11. The image input device as set forth in claim 10, in which said image forming means is implemented by a two-dimensional array of gradient index lenses.

12. The image input device as set forth in claim 1, in which said image forming means and said image pick up device are respectively implemented by a linear array of gradient index lenses and a linear image sensor, and said image input device further comprises a carrier for supporting said linear array of gradient index lenses and said linear image sensor and a driving unit for moving said carrier in a perpendicular direction of a longitudinal direction of said finger.

13. An image input device for producing a piece of data information representative of a fingerprint of a finger of a living body, comprising:
   a transparent optical guide plate including a first surface having an detecting area where said living body presses said finger, and radiating a reflection representative of an image of said fingerprint from a second surface to the outside thereof;
   a light source radiating light into said transparent optical guide so as to illuminate said detecting area;
   an image pickup device provided in the vicinity of said second surface, and having an incident surface so as to detect said reflection;
   a gradient index lens array provided between said second surface and said image pickup device so as to form said image on said incident surface; and
   a case for accommodating said transparent optical plate, said light source, said image pickup device and said image forming mean.

14. The image input device as set forth in claim 13, in which said light source includes one of a light emitting diode, an electro-luminescence plate and a cold cathode tube and reflecting layers for confining said light in said transparent optical guide plate.

15. The image input device as set forth in claim 13, in which said case has an inner space photo-shielded from an external light and a window open to the outside of said inner space, and said transparent optical plate, said light source, said image pickup device and said image forming mean are accommodated in said inner space in such a manner that said transparent optical plate is exposed to said window.

16. The image input device as set forth in claim 15, in which said case is colored in black.

17. An image input device for producing a piece of data information representative of a fingerprint of a finger of a living body, comprising:
   a transparent optical guide plate including a first surface having an detecting area where said living body presses said finger, and radiating a reflection representative of an image of said fingerprint from a second surface to the outside thereof;
   a light source radiating light into said transparent optical guide so as to illuminate said detecting area;
   an image pickup device provided in the vicinity of said second surface, and having an incident surface so as to detect said reflection;

an image forming means provided between said second surface and said image pickup device so as to form said image on said incident surface;

a case for accommodating said transparent optical plate, said light source, said image pickup device and said image forming mean; and an eliminating means for eliminating a sub-piece of data information representative of a sub-image of valley lines of said fingerprint from said piece of data information representative of said fingerprint.

18. The image input device as set forth in claim 17, in which said eliminating means is implemented by a filter for eliminating a low frequency component from an image carrying signal representative of said image.

19. The image input device as set forth in claim 17, in which said eliminating means is implemented by an anti-reflecting layer attached to said second surface so as not to allow said reflection to illuminate valley lines of said fingerprint.

20. The image input device as set forth in claim 17, in which said case has an inner space photo-shielded from an external light and a window open to the outside of said inner space, and said transparent optical plate, said light source, said image pickup device and said image forming mean are accommodated in said inner space in such a manner that said transparent optical plate is exposed to said window.

21. The image input device as set forth in claim 20, in which said case is colored in black.

22. The image input device as set forth in claim 20, in which said light source, said image pickup device and said image forming means are respectively implemented by at least one light emitting diode, an area image sensor and a gradient index lens array.

23. An image input device for producing a piece of data information representative of a fingerprint of a finger, comprising:

a transparent optical guide plate including a first surface having an detecting area where said finger is pressed, and radiating a reflection representative of an image of said fingerprint from a second surface to the outside thereof;

a light source radiating light into said transparent optical guide so as to illuminate said detecting area;

an image pickup device provided in the vicinity of said second surface, and having an incident surface so as to detect said reflection;

a gradient index lens array provided between said second surface and said image pickup device so as to form said image on said incident surface;

a case for accommodating said transparent optical plate, said light source, said image pickup device and said image forming mean; and a biological information discriminating means checking said reflection to see whether or not said finger changes the reflective index with time so as to produce another piece of data information representative of a living body or non-living body.

24. The image pickup device as set forth in claim 23, in which said biological information discriminating means includes a relieving means formed in said detecting area for relieving a part of said finger from the pressure against said detecting area, a coloring means for making said image colored, a data storing means for storing a first set of video data representative of said image at a first timing, and a comparing means comparing said first set of video data with a second set of video data representative of said image at a second timing after said first timing to see whether or not said image is changed in color for producing said another piece of data information.

25. The image input device as set forth in claim 23, in which said case has an inner space photo-shielded from an external light and a window open to the outside of said inner space, and said transparent optical plate, said light source, said image pickup device and said image forming mean are accommodated in said inner space in such a manner that said transparent optical plate is exposed to said window.

26. The image input device as set forth in claim 25, in which said case is colored in black.

27. The image input device as set forth in claim 23, in which said light source, said image pickup device and said image forming means are respectively implemented by at least one light emitting diode, an area image sensor and a gradient index lens array.

* * * * *